United States Patent
Lugert

(10) Patent No.: US 6,316,526 B1
(45) Date of Patent: Nov. 13, 2001

(54) METHOD FOR MAKING LEADS FOR COLOR PENCILS, COSMETIC PENCILS AND COLORED CHALK

(75) Inventor: Gerhard Lugert, Nürnberg (DE)

(73) Assignee: A.W. Faber-Castell Unternehmensverwaltung GmbH & Co., Stein (DE)

( * ) Notice: Subject to any disclaimer, the term of this patent is extended or adjusted under 35 U.S.C. 154(b) by 0 days.

(21) Appl. No.: 08/954,161

(22) Filed: Oct. 20, 1997

(30) Foreign Application Priority Data

Oct. 30, 1997 (DE) ................................. 196 43 356

(51) Int. Cl.⁷ ....................................... C08D 13/00
(52) U.S. Cl. ............................................. 523/164
(58) Field of Search .............................. 523/164

(56) References Cited

U.S. PATENT DOCUMENTS 2,784,164  3/1957  Ahlman et al. .
5,360,281  11/1994  Kamen et al. .

FOREIGN PATENT DOCUMENTS

| | | |
|---|---|---|
| 2442983C2 | 11/1978 | (DE) . |
| 3120241C2 | 12/1985 | (DE) . |
| 4214396A1 | 11/1992 | (DE) . |
| 4230793A1 | 3/1994 | (DE) . |
| 0697447A1 | 2/1996 | (EP) . |

*Primary Examiner*—Edward J. Cain
(74) *Attorney, Agent, or Firm*—Venable; Gabor J. Kelemen

(57) ABSTRACT

A simplified method for producing a lead for color pencils, cosmetic pencils and colored chalk with good down stroke behavior involves mixing powdered or granular base materials containing a thermolabile, polymeric binding agent, inorganic filler materials and a coloring agent with water and then extruding the mixed materials to form raw leads, which extruded material is subsequently heat treated at the binding agent decomposition temperature for a time sufficient to partially decompose the binding agent. Enough water is mixed with the base material to achieve a lead mass of approximately 5 parts by weight of base material and 1 part by weight of water.

19 Claims, No Drawings

METHOD FOR MAKING LEADS FOR COLOR PENCILS, COSMETIC PENCILS AND COLORED CHALK

The invention relates to a method for producing leads for color pencils, cosmetic pencils and colored chalks. As a rule, such leads contain a binding agent, e.g. a cellulose derivative, filler materials such as kaolin and coloring agents. For producing leads, the base materials are mixed with water, e.g. in a plasticizer, to form a lead mass. Raw leads are extruded from this lead mass and are dried at temperatures of approximately 110° C. The consistency or hardness of a lead is determined decisively by the binding agent used and its concentration. In addition, the mechanical stability and consistency of a lead depends on the additives, in particular also the filler materials. Traditional leads are dipped into liquid waxes, liquid fats or fatty acids following the drying to improve the downstroke behavior. A wax absorption of between approximately 15% and 25% of the total weight of the lead is necessary to change the downstroke behavior of the leads noticeably in the direction of a softer downstroke. Adding emulsifying agents, fats, waxes and fatty acids to the base materials already provides another option of improving the downstroke behavior of the raw leads. The improved downstroke behavior is thus always obtained with the aid of a relatively high share of fats, waxes, fatty acids or emulsifying agents. However, for some types of uses, such a high share of the aforementioned materials is not desirable. Reducing the share of binding agent provides another option for influencing the downstroke behavior. This is linked however to a reduction in the mechanical stability of the raw leads. There is an increased danger of breakage before the raw leads with little binding agent have reached their final stability, thereby resulting in increased rejection rates caused by lead breakage.

Based upon this, it is the object of the invention to propose a method for producing leads for color pencils, cosmetic pencils and colored chalks, which permits varying the mechanical qualities and in particular the downstroke behavior of the leads in a simple way through production technology.

The solution is with a method according to claim 1. Based on this, the crushed base materials, having a somewhat powder-like or granular shape and containing a thermolabile, polymeric binding agent, inorganic filler materials, and coloring agents, are mixed with water. The resulting raw material mass is subsequently extruded into raw leads and these are heat-treated at a raised temperature, namely a decomposition temperature, until the binding agent is partially decomposed. The finished lead consequently contains a polymeric binding agent that is partially decomposed as a result of a thermal treatment step. In addition to the above-mentioned factors, such as weight share and type of binding agent, which influence the firmness and downstroke behavior, this provides another option of influencing the downstroke behavior in particular. That is, the binding agent matrix holding together the lead constituents can be changed through the degree of its thermal decomposition. Thus, varied consistencies and mechanical stabilities as well as a varied downstroke behavior can be achieved, for example, by changing only the thermal decomposition degree for leads having an otherwise comparable composition. In addition, leads are made available that display a soft downstroke with sufficient lead mass release to the underlying material, despite the lack of a high share of fat and wax, which normally determines the downstroke behavior. Depending on the respectively used binding agent, the consistency and the downstroke behavior of the lead are essentially determined by the temperature level and the duration of the treatment. As mentioned in the above, it is not easily possible to reduce the share of binding agent in the raw lead mass with the lead-production methods in question. A reduced share of binding agent would result in increased lead breakage owing to the mechanical drawbacks during the extrusion of the raw leads, as well as the subsequent transport to a drying station or a heat-treatment station. The method according to the invention is based on the idea of reducing, as it were, the share of binding agent in a finishing processing step, in which the leads are subjected to a heat-treatment without mechanical influencing, or of weakening, as it were, the effectiveness of the binding agent, thereby changing the downstroke behavior of the lead. It is thus possible to completely forego a modification of the downstroke behavior through dipping the finished lead into waxes or fats. However, such a measure can be useful if the heat-treated lead must be modified in the direction of a softer downstroke behavior. In that case, only small amounts of wax or fat are necessary.

It is preferable if biopolymers from the group of cellulose derivatives and alginates are used as binding agents. Alginates are understood to be salts and esters of the alginic acid. Such binding agents have a high binding power for the lead constituents. However, one essential advantage of these binding agents is their thermal decomposability, wherein the extent of the decomposition can be adjusted in fine degrees via the temperature level (in the following called decomposition temperature) and the duration of the heat treatment.

The following base materials (amounts given in percentages by weight) are preferably used: 0.5%–12.5% binding agent; 30%–90% filler material; 5%–96% coloring agent. If necessary, it is possible to add up to 2% of waxes, fats, fatty acids and/or emulsifying agents and up to 10% of auxiliary agents. The base materials are mixed with an amount of water that is sufficient to obtain an extrudable mass. It is preferable if enough water is added to the base materials, so that the mixture contains approximately 5 parts by weight of base material and 1 weight share of water. The finished leads contain less than 1% water owing to the heat treatment or the drying.

Natural magnesium silicates, kaolin, finely-ground quartz and pumice powder, talcum and mica are preferably used as filler materials. Mica in this case is understood to include alkali, hydroxyl and even fluorine-containing aluminosilicates, which belong to the phyllosilicates. Inorganic or organic pigments, colorants or pigmented colorants as well as coated or non-coated metal bronzes can be used as coloring agents. Coated metal bronzes are understood to be those, for which the metal particles have a coating of, for example, silicon dioxide. Traditional surfactants, glycols, alcohols, fats or fatty acids, waxes and emulsifying agents can be used as auxiliary agents. The fats, waxes, fatty acids and emulsifying agents can be added to the lead base mixture with a share of 2 weight %. Larger amounts of these materials are not retained by the lead matrix, owing to their liquefaction during the heat treatment, but can be added after the heat treatment with a share of up to 25 weight % through dipping into the liquefied waxes, fats, fatty acids and emulsifying agents. However, it is also conceivable that following their production in the standard way, the leads according to the invention are dipped into melted waxes, fats or fatty acids to further improve, if necessary, the soft downstroke behavior caused by the partially decomposed binding agent. However, a smaller share than for traditional leads is necessary for this.

The heat treatment for the method according to the invention can last up to 24 hours, depending on the base materials used, the level of the decomposition temperature, and the desired degree of decomposition of the binding agent.

The binding agent preferably is composed of at least one material selected from the group hydroxyethylcellulose, methyl hydroxyethylcellulose, ammonium carboxymethylcellulose, alkali carboxymethylcellulose and alginates.

With a method according to the invention, the raw leads produced are preferably dried at a drying temperature of 30° C. to 110° C. prior to the heat treatment that partially decomposes the binding agent. The heat treatment follows only after this drying step. Both processing steps can be carried out in one and the same heating furnace, wherein a correspondingly low temperature is maintained during the drying phase. It has turned out during the heat treatment that best results are obtained if a constant decomposition temperature is maintained essentially during the complete duration of the heat treatment. In some cases, however, it may be useful to have temperature stages, wherein the respective temperature in each stage is held to a constant level.

The invention is explained in more detail in the following with the aid of examples:

EXAMPLE 1

The production of a blue, cylindrical, colored lead with a lead diameter of 3.8 mm.

Composition of the lead mass:

| | |
|---|---|
| sodium carboxymethylcellulose | 0.6 g |
| kaolin | 176.0 g |
| copper phthalocyanine blue Pigment Blue 15 C.I. No. 74160) | 18.0 g |

For the production, the powdered components are initially mixed homogeneously with 40 ml water. Leads are extruded from the resulting lead mass, and these are dried at 40° C. for approximately 12 hours. Following that, the raw leads are tempered at a constant temperature of 180° C. for 20 minutes.

The resulting leads have a downstroke behavior that is clearly improved relative to the raw leads. That is, the leads show a good lead material release on paper and have a gliding, soft downstroke. The breaking resistance of the leads is reduced by only about 10% as compared to the raw leads.

EXAMPLE 2

The production of a wine-red, cylindrical colored lead with a diameter of 4.3 mm.

Composition of the lead mass:

| | |
|---|---|
| methyl hydroxyethylcellulose | 4.0 g |
| finely ground quartz powder | 60.0 g |
| pumice powder | 60.0 g |
| talcum | 40.0 g |
| iron oxide pigment (Pigment Red 101 CAS No. 1309-371) | 5.0 g |
| azoic red pigment (Pigment Red 170 C.I. No. 12475) | 6.6 g |

-continued

| | |
|---|---|
| soot (pigment Black 7 C.I. No. 77266) | 0.6 g |
| stearic acid | 2.0 g |
| glycerine | 2.0 g |
| zinc sulfide/barium sulfate pigment CAS No. 1345-05-07) | 19.8 g |

According to example 1, raw leads are initially produced and these are subjected to microwave radiation at 850 watt for 20 minutes.

The downstroke of the lead obtained in this way is clearly softer than the downstroke of the raw lead. The breaking strength of the lead is reduced by approximately 15% as compared to the original raw leads.

EXAMPLE 3

The production of a light blue, cylindrical colored lead having a diameter of approximately 4.3 mm.

Composition of the lead mass:

| | |
|---|---|
| methyl hydroxyethylcellulose | 4.0 g |
| finely ground quartz powder | 60.0 g |
| pumice powder | 60.0 g |
| zinc sulfide/barium sulfate pigment (CAS No. 1345-05-07) | 10.0 g |
| finely ground titanium dioxide (Rutil) | 13.0 g |
| copper phthalocyanine blue (Pigment Blue 15:3, C.I. No. 74160) | 1.0 g |
| ultramarine blue (Pigment Blue 29, C.I. No. 77007) | 8.0 g |
| Japan wax | 2.0 g |
| glycerine | 2.0 g |

The mass is processed into raw leads in the same way as in Example 1. The resulting leads show a light blue downstroke on paper, with a satisfactory lead material release. If these leads are tempered at 230° C. for 20 minutes, the resulting breaking strength is reduced by slightly more than 20%. These leads simultaneously have a very soft, good downstroke and excellent release on paper.

EXAMPLE 4

The production of a skin-colored, powdery lead for makeup and cosmetic applications with a diameter of approximately 4.5 mm.

Composition of the lead mass:

| | |
|---|---|
| hydroxyethylcellulose | 1.0 g |
| methyl hydroxyethylcellulose | 3.0 g |
| talcum | 140.0 g |
| magnesium myristate | 6.0 g |
| titanium dioxide | 40.0 g |
| iron oxide (Pigment Red 110 CAS No. 1309-37-1) | 10.0 g |

The mass is mixed homogeneously with approximately 40 g water in the plasticizer and is processed into raw leads in accordance with Example 1. The resulting leads are tempered initially for 1 hour at 230° C. and subsequently for 1 hour at 240° C. Leads with a powder-type downstroke are obtained.

EXAMPLE 5

The production of a flesh-colored, powder-type lead for makeup and cosmetic purposes, having a diameter of approximately 4.3 mm.

Composition of the lead mass:

| | |
|---|---|
| methyl hydroxyethylcellulose | 20.0 g |
| magnesium myristate | 6.0 g |
| titanium dioxide | 40.0 g |
| mica | 140.0 g |
| iron oxide (Pigment Red 101 CAS No. 1309-37-1) | 10.0 g |

The powdery base materials are initially dried, then mixed homogeneously with approximately 45 g water and extruded as raw leads as in Example 1. The raw leads thus obtained are tempered evenly for 30 minutes at approximately 260° C., resulting in powdery leads suitable for cosmetic purposes.

EXAMPLE 6

The production of a pink-colored lead, which is suitable for makeup purposes as well as for use on paper. The lead diameter is approximately 4.3 mm.

Composition of the lead mass:

| | |
|---|---|
| methyl hydroxyethylcellulose | 3.8 g |
| talcum | 140.4 g |
| magnesium myristate | 6.0 g |
| titanium dioxide | 40.0 g |
| D + C Red 7 (C.I. 15850) | 14.0 g |

Initially, raw leads are produced the same way as in Example 1 by adding approximately 40 g water. The raw leads are tempered 245° C. for 30 minutes. This results in leads showing an even downstroke on paper and which are also suitable for the coloring skin (cosmetic uses).

What is claimed is:

1. A method for producing a lead for color pencils, cosmetic pencils and colored chalk comprising a) mixing crushed base materials, having an approximately powdered or granular form and containing thermolabile, polymeric binding agent, inorganic filler materials and a coloring agent with water; b) extruding the resulting raw material mass-water mixture to form raw leads; and c) heat treating the raw leads at a binding agent decomposition temperature, until the binding agent is partially decomposed.

2. A method according to claim 1, characterized in that cellulose derivatives or alginates are used as binding agent, and the raw leads are heat-treated at a temperature of 150° C. to 350° C.

3. A method according to claim 2, characterized in that alkali carboxymethylcellulose, ammonium carboxymethylcellulose, hydroxyethylcellulose, methyl hydroxyethylcellulose and/or alginates are used as binding agents.

4. A method according to claim 3, characterized by a heat treatment lasting from 10 minutes to 24 hours.

5. A method according to claim 1, characterized in that the raw leads are dried prior to the processing step c).

6. A method according to claim 5, characterized by a drying temperature of 30° C. to 110° C.

7. A method according to claim 1, characterized by a decomposition temperature that essentially remains constant during essentially the complete duration of the heat treatment.

8. A method according to claim 1, characterized by temperature stages for the heat treatment, wherein a lower decomposition temperature is used in the first stage and a higher decomposition temperature in the second stage.

9. A method according to claim 1, characterized by the use of the following base materials (percentages by weight):

| | |
|---|---|
| 0.5%–12.5% | binding agents |
| 30%–90% | filler materials |
| 5%–96% | coloring agents |
| 0%–2% | waxes, fats, fatty acids and/or emulsifying agents |
| 0%–10% | auxiliary agents |

10. A method according to claim 9, characterized in that the base materials are mixed with enough water, so that the lead mass contains approximately 5 parts by weight of base material and 1 part by weight of water.

11. A method according to claim 1, characterized by the use of a biopolymeric material from the group of cellulose derivatives and alginates as binding agent.

12. A method according to claim 1, characterized by the use of a binding agent, which is selected from the group of alkali carboxymethylcellulose, ammonium carboxymethylcellulose, hydroxyethylcellulose and methyl hydroxyethylcellulose.

13. A method according to claim 1, characterized by the use of at least one filler material from the group of natural magnesium silicates, kaolin, quartz powder, pumice powder, talcum, ground clay and mica.

14. A method according to claim 1, characterized by the use of at least one coloring agent from the group inorganic or organic pigments, colorants, pigmented colorants, metal bronzes, and coated metal bronzes.

15. A method according to claim 1, characterized by the use of at least one auxiliary agent from the group surfactants, glycoles, alcohols, fats, fatty acids, waxes, and emulsifying agents.

16. A method according to claim 8, characterized in that the heat-treated leads are dipped into fats, waxes, fatty acids and/or emulsifying agents and are saturated with these materials.

17. A method according to claim 8, characterized in that fats, waxes, fatty acids and/or emulsifying agents are added to the base materials.

18. A method according to claim 17, characterized in that up to 2 weight % in waxes, fats, fatty acids and/or emulsifying agents are added.

19. A method according to claim 16, characterized in that the share of waxes, fats, fatty acids and/or emulsifying agents is up to 25 weight % following the dipping.

\* \* \* \* \*